United States Patent [19]

Hjertman et al.

[11] Patent Number: 5,769,824
[45] Date of Patent: Jun. 23, 1998

[54] APPARATUS FOR CONTROLLED DELIVERY OF LIQUIDS

[75] Inventors: Birger Hjertman, Vällingby, Sweden; Peter Michel, Burgdorf, Switzerland

[73] Assignee: Pharmacia & Upjohn Aktiebolag, Stockholm, Sweden

[21] Appl. No.: 500,383

[22] Filed: Mar. 26, 1993

Related U.S. Application Data

[63] Continuation of Ser. No. 965,267, filed as PCT/SE91/00506 Jul. 25, 1991, abandoned.

[51] Int. Cl.⁶ .................................................. A61M 37/00
[52] U.S. Cl. ........................ 604/143; 604/131; 604/141; 604/91
[58] Field of Search ............................ 604/81–5, 89–91, 604/131, 140–1, 143, 146–7, 149, 152, 181–3, 187, 218, 221, 228, 233–4, 246, 249, 256; 222/386, 389

[56] References Cited

U.S. PATENT DOCUMENTS

| | | | |
|---|---|---|---|
| 3,881,484 | 5/1975 | Gidcumb, Jr. ............................ | 604/89 |
| 4,744,786 | 5/1988 | Hooven .................................. | 604/143 |
| 4,822,340 | 4/1989 | Kamstra .................................. | 604/89 |
| 4,874,381 | 10/1989 | Vetter ...................................... | 604/91 |
| 5,135,500 | 8/1992 | Zdeb ...................................... | 604/143 |

Primary Examiner—Michael Buiz
Assistant Examiner—Jennifer R. Sadula
Attorney, Agent, or Firm—Pollock, Vande Sande & Priddy

[57] ABSTRACT

An apparatus for controlled delivery of a liquid consists of a delivery unit which comprises a liquid container (3) having at least one movable wall (12) and a liquid outlet which is provided with a flow restriction, and a power unit which comprises a second container (21) which also has at least one movable wall (29) and wherein a vacuum may be established, and a mechanical coupling (31) between the movable wall (12) of the liquid container (3) and the movable wall (29) of the second container (21). The delivery unit and the power unit are connected together coaxially when the apparatus is prepared for delivery, and in this connecting together, the movable wall (29) of the second container is displaced by means of the mechanical coupling (31) such that the vacuum is established. The ambient atmospheric pressure then acts against this vacuum, and this pressure is transmitted by the mechanical coupling (31), which is directly acting on the movable wall (12) of the liquid container (3) such that the liquid is forced out through the outlet (4) and the restriction therein.

17 Claims, 6 Drawing Sheets

APPARATUS FOR CONTROLLED DELIVERY OF LIQUIDS

CROSS REFERENCE TO RELATED APPLICATION

This is a continuation of application Ser. No. 07/965,267, filed Jan. 26, 1993, now abandoned, which was a 371 of PCT/SE91/00506.

TECHNICAL FIELD

The present invention relates to the field of delivery of fluids, and more exactly to an apparatus for the controlled delivery of liquids. Especially, the invention refers to an apparatus for the controlled delivery of liquids which are to be administered to humans or animals by parenteral injection or infusion.

BACKGROUND OF THE INVENTION

In many cases, it is desirable to administer a liquid to a patient in a controlled manner for an extended period of time, such as one hour or more. This is the case in, for instance, parenteral nutrition, and also in the treatment of certain conditions such as cardiac infarct, where a solution of streptokinase may be administered in a uniform and controlled manner for a time of 30 minutes or more. This is not a great problem in the hospital, where infusion stands may be used, where the liquid is administered by gravity, or by infusion pumps of various designs.

However, problems arise when such an infusion or injection is to be carried out under ambulant conditions, such as in an emergency treatment of a cardiac infarct. In such cases, infusion stands based on gravity feed are cumbersome and inconvenient, and conventional infusion pumps are dependent on an external power source, and are also inconvenient to carry around.

There are also cases where an injection has to be given quickly and without delay, often by the patient to himself. In such cases there is a need for a powered injection device, which can administer a determined amount of an agent quickly and without further intervention from the patient.

Thus, there exists an important need for a device for a controlled parenteral administration of a liquid for a determined time, which is easy to transport, independent of external power sources, and fulfills the conventional safety requirements regarding freedom from bacterial contamination, freedom from enclosed air and the like.

Various infusion devices are known which as a power source utilize a gas generating material, such as a hydrocarbon or fluorocarbon which has a suitable volatility. The liberated gas acts on a piston which is connected to a plunger in an infusion syringe containing the liquid to be infused, and in this way forces the liquid out through a line to the patient. The flow of the liquid is controlled through a suitable constriction in the outflow line. These devices, however, have a number of shortcomings. The volatility of the gas-generating material is dependent on the ambient temperature, and thereby also the gas pressure which acts as the driving force for the delivery of the liquid. This makes the rate of delivery vary with the temperature, which is usually highly undesirable. Furthermore, the release of hydrocarbons and especially fluorocarbons to the atmosphere is not unobjectionable from an environmental point of view. Finally, there may be in some types of apparatus a risk that the liquid to be administered is contaminated by the driving gas, for instance if a piston leaks.

Therefore, devices have recently been developed which are not dependent on the generation of gas as a driving force, but instead on the pressure of the atmosphere acting against a vacuum. Such devices are described in GB-A-2,195,894 and U.S. Pat. No. 4,180,067.

GB-A-2,195,894 discloses an infusion device which comprises a power section which in use is connected to a syringe section. The power section comprises a first chamber which contains a viscous liquid, and a second chamber which is under a vacuum. When the device is to be actuated, a metering orifice is opened between the first and the second chamber in the power section, so that the ambient air pressure acting on a piston will force the viscous liquid through the metering orifice into the vacuum chamber at the same time as the plunger of the syringe is forced outwards to discharge the liquid to be dispensed. Through the viscous liquid acting as a damper, the delivery of liquid from the syringe may be controlled by varying the size of the metering orifice.

This device has a number of shortcomings. Its construction is rather complicated and is therefore expensive, especially as the device is only intended to be used once before being discarded. Also, there is a risk that small leaks will make the device inoperative, as the power section is set under vacuum already at its manufacture, and may be stored for a considerable time before it is used.

U.S. Pat. No. 4,180,067 discloses an apparatus for delivering a fluid at a controlled rate from a container. The apparatus comprises a frame for holding the container in a cavity and a cylinder arranged in the frame and closed at one end. A piston is slidably arranged in the cylinder such that when the piston is near the open end of the cylinder, there is a vacuum in the cylinder and the ambient air pressure acts to drive the piston into the cylinder. When the piston is at its outermost position and the vacuum has been estabilshed, it can be coupled to a movable wall in the container for fluid such that the movement of the piston into the cylinder under the influence of the ambient air pressure also displaces the movable wall so that the fluid is forced out of the container. By a suitable flow restrictor valve in the fluid outlet, the fluid flow from the container may be controlled such that a desired delivery rate is attained.

In a preferred embodiment, the frame comprises a second cylinder with a piston. This second cylinder is filled with an auxiliary fluid, and its piston is coupled to the piston in the first cylinder in such a way that the movement of the first piston under the influence of the ambient air pressure also displaces the second piston to urge the auxiliary fluid out of the second cylinder through a suitable flow restrictor valve. In this way, the movement of the first piston is controlled such that a desired delivery rate is attained.

This apparatus has the advantage that the vacuum is not established until shortly before the fluid is to be delivered, and that it can be re-used with a new fluid container as many times as desired. However, its construction is rather complicated, which makes the apparatus costly and cumbersome to use.

SUMMARY OF INVENTION

Through the present invention, an apparatus for controlled delivery of fluids is provided, which eliminates the drawbacks associated with the previously known devices for this purpose. The apparatus of the invention is especially suitable for the controlled delivery of liquids which are to be administered to humans or animals by parenteral injection or infusion, although it is not restricted to this use.

According to the invention, an apparatus for the controlled delivery of a liquid is provided, which consists of a delivery unit which comprises a liquid container and which has at least one movable wall and a liquid outlet which is provided with a flow restriction, and a power unit which comprises a second container which also has at least one movable wall and wherein a vacuum can be established, and a mechanical coupling between the movable wall of the liquid container and the movable wall of the second container. The delivery unit and the power unit are connected together coaxially to prepare the apparatus for delivery, and in said connecting together, the movable wall of the second container is displaced by means of the mechanical coupling such that the vacuum is established and the ambient atmospheric pressure acts against the vacuum, and this pressure is transmitted by the mechanical coupling, which is directly acting on the movable wall of the liquid container, such that the liquid is forced out through the outlet and the restriction therein.

In a preferred embodiment, the movable walls consist of pistons or plungers, and the mechanical coupling is a rod, which connects the pistons or plungers. One or both of the movable walls may also be in the form of a membrane.

In a further embodiment, the flow restriction consists of an adjustable flow restrictor valve, so that the flow from the outlet may be varied.

BRIEF DESCRIPTION

DESCRIPTION OF BEST AND VARIOUS MODES FOR CARRYING OUT INVENTION

In the figures of the drawing, like parts have the same reference numbers.

Figure 1:
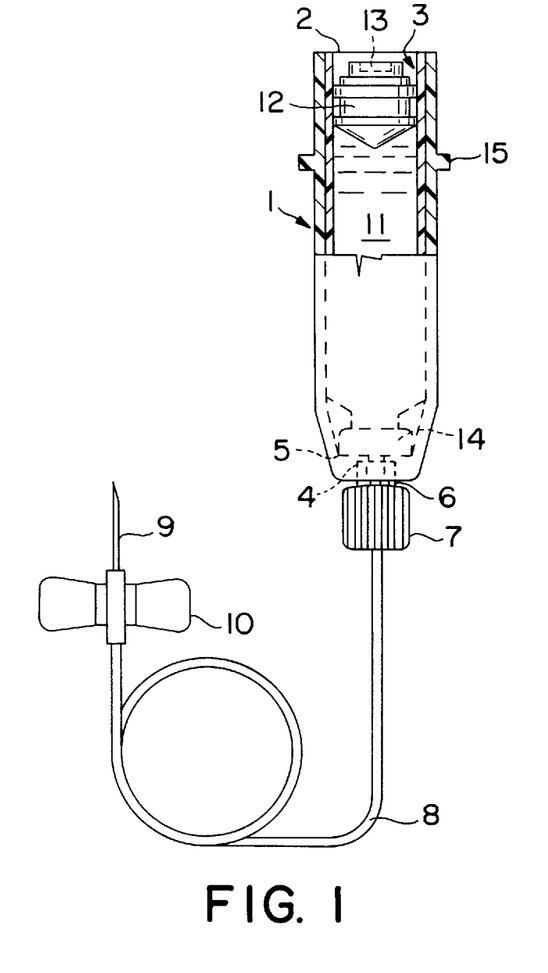
FIGS. 1 and 2 represent partial cross-sectional views of an embodiment of an apparatus according to the present invention in two parts, prior to assembly.
Figure 2:
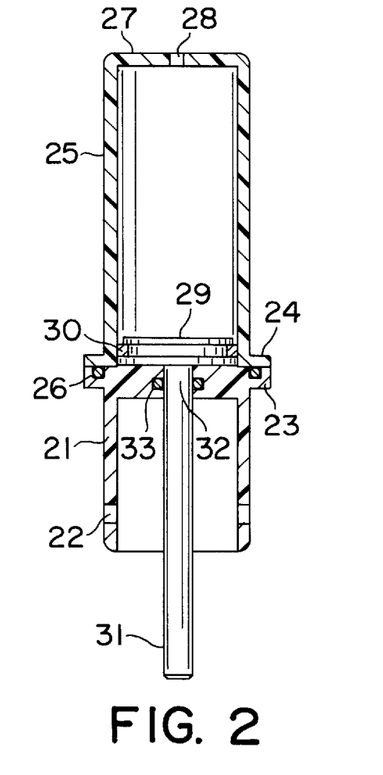

The apparatus comprises two units, a delivery unit, which is shown in FIG. 1, and a power unit, which is shown in FIG. 2.

FIG. 1 shows a partly sectional view of the delivery unit of the apparatus of the invention.

The delivery unit comprises a sleeve 1, which has an opening 2, through which may be inserted an injection cartridge 3. At its other end, the sleeve 1 has a smaller opening 4 and an internal flange 5, against which the outlet end of the cartridge 3 rests. The smaller opening 4 is provided with a threaded connecting tube 6, onto which is screwed a threaded connecting piece 7. As shown in FIG. 1, this connecting piece 7 assures the connection between the smaller opening 4 of the sleeve 1 and a flexible tube 8, which at its other end is connected to a hypodermic needle 9. An adhesive tape 10 is provided for securing the needle assembly to the skin of the patient. It is of course also possible to connect the needle 9 directly to the connecting piece 7 without any intervening tube.

The injection cartridge 3 may be of a conventional construction. It contains a liquid 11 to be injected, and is closed at its rear end by a plunger or piston 12. This plunger may have a recess 13 at its rear end for receiving a connecting rod, as will be more closely explained hereinafter.

At its front end, the injection cartridge 3 is closed in a conventional way by a rubber septum which is held in place by a metal capsule 14. The connection between the cartridge 3 and the tube 8 via the connecting piece 7 also comprises a hollow needle (not shown), which in a known way pierces the rubber septum such that a liquid connection is established between the interior of the cartridge and the tube 8 with the needle 9.

In the drawing, the injection cartridge 3 is shown as a simple, single-chamber cartridge. However, it may also be a dual-chamber cartridge containing a dry active substance in one of the chambers and a liquid in the other, the two chambers being separated by a movable wall. Usually, the dry substance is in the front chamber and the liquid in the rear one. In the wall of the cartridge is arranged a bypass channel which may be operative or inoperative, depending on the position of the movable wall.

When the dual-chamber cartridge is to be made ready for use, the rear plunger is moved forward and will then also displace the liquid in the rear chamber forward. As the liquid is largely incompressible, it will in its turn urge the movable wall forward until it is in such a position that the rear opening of the bypass channel is exposed to the liquid. The further movement of the rear plunger will then force the liquid through the bypass channel into the front chamber to dissolve the dry substance.

This arrangement is very suitable for the administering of substances which are too unstable to be stored in the form of a solution, such as certain hormones and proteins. In this way, the solution is not prepared until immediately before it is to be administered, and the mixing process can be made very careful for delicate substances. The use of a dualchamber cartridge is a preferred embodiment of the invention.

An important feature of the apparatus of the invention is that a flow restriction is arranged in the flow path of the liquid from the injection cartridge 3 to the hypodermic needle 9. This restriction may be arranged in the connecting piece 7 and may, for example, be a constriction, such as a capillary in the flow path of the liquid. The diameter of the constriction is adapted to the liquid to be injected such that a suitable flow is obtained. This adaption can be carried out by a person skilled in the art on the basis of simple routine tests.

The flow restriction may also be arranged in other ways. Thus, the tube 8 and/or the needle 9 for administering may themselves be of such dimensions that they act as a suitable restriction.

The flow restriction may also be adjustable, and may, for instance, be arranged as an adjustable clamp on the flexible tube 8.

The sleeve 1 is also provided with means for joining the delivery unit to the power unit shown in FIG. 2. These means may be arranged as a bayonet lock 15. Other arrangements for the joining are also possible, such as a snap joint or a threaded joint for screwing the two units together. It is important that the joint is secure, but yet can be released when desired.

FIG. 2 is a sectional view of the power unit of the apparatus of the invention. This section comprises a sleeve 21 which is arranged to fit snugly over the upper part of the sleeve 1 of the delivery unit shown in FIG. 1. Means 22 are provided to cooperate with the means 15 (FIG. 1) to lock the two sleeves releasably together, such as by a bayonet lock.

The sleeve 21 is closed at its upper end by an end wall 23, which is shaped as a flange. To this flange is releasably attached the flange 24 of a cylinder 25. An airtight seal between the two flanges is assured by a sealing ring 26.

The cylinder 25 is closed at its upper end by a wall 27, wich may be integral with the cylinder. This wall 27 is provided with an orifice 28, which permits the passage of air between the interior of the cylinder and the ambient atmosphere.

Inside the cylinder 25 is arranged a piston or plunger 29, which is in sealing contact with the interior wall of the cylinder via the sealing ring 30. In its resting position, the piston rests on the upper surface of the end wall 23 of the sleeve 21.

To the underside of the piston is attached a connecting rod 31, which sealingly traverses the end wall 23 through an orifice 32. An airtight seal between the connecting rod 31 and the wall of the orifice 32 is assured by the sealing ring 33.

Thus, when the connecting rod 31 and the piston 29 are moved upwards, there will be a vacuum established in the cylinder 25 below the piston 29, while the atmospheric pressure will prevail in the cylinder above the piston, as this part of the cylinder is connected to the ambient atmosphere through the orifice 28.

Figure 3:
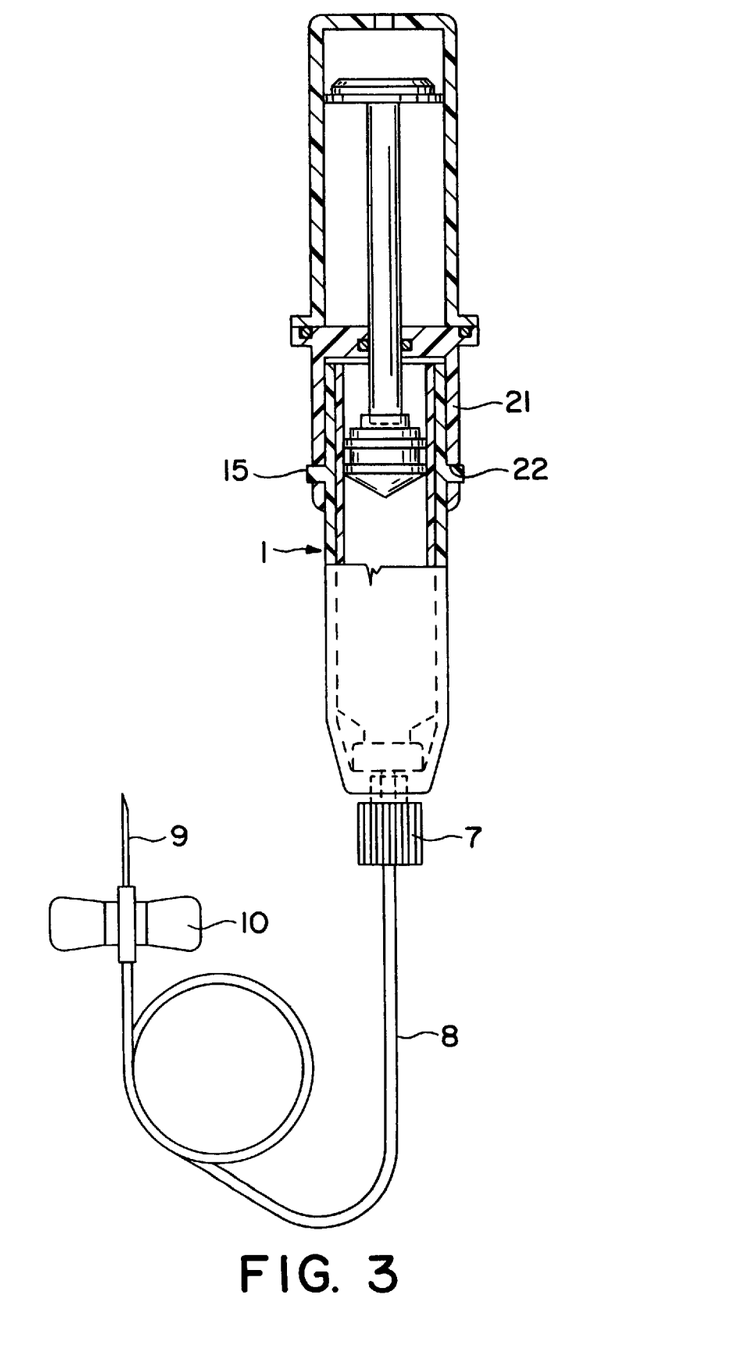
FIG. 3 represents a partial cross-sectional view of the embodiment of the present invention illustrated in FIGS. 1 and 2 in an assembled state, ready for use.

FIG. 3 shows the apparatus of the invention in an assembled state and ready for use. The sleeve 21 of the power unit has been placed around the upper part of the sleeve 1 of the delivery unit, and the two sleeves have been locked securely together by means of the bayonet lock 15, 22.

When the two sleeves 1, 21 are coaxially brought together, the lower end of the piston rod 31 will engage the recess 13 in the rear end face of the plunger 12 of the injection cartridge 3, to rest securely in said recess. The rod 31 and the piston 29 will then be moved upwards in the cylinder 25 as the two sleeves are brought together, so that a space will be established in the cylinder under the piston 29. Because of the seals made by the sealing rings 26, 30 and 33, no air can enter this space, so that a vacuum will be established therein. On the other side of the piston 29, the atmospheric air pressure acts on the piston, as the cylinder on this side is in connection with the ambient atmosphere through the orifice 28.

When the two sleeves 1, 21 have been locked together by means of the bayonet lock 15, 22, the piston 29 will be at its highest position in the cylinder 25. In the space below the piston in the cylinder, there will be a substantially complete vacuum, as the piston in its initial position has rested on the end wall 23 of the sleeve 21, and there is essentially no space below it.

The atmospheric pressure will now act on the upper side of the piston 29 to force it downwards, and this force will be transmitted by the rod 31 to act on the upper side of the plunger 12 in the injection cartridge 3 to force the liquid 11 in the cartridge out through the tube 8 and the needle 9.

Figure 10:
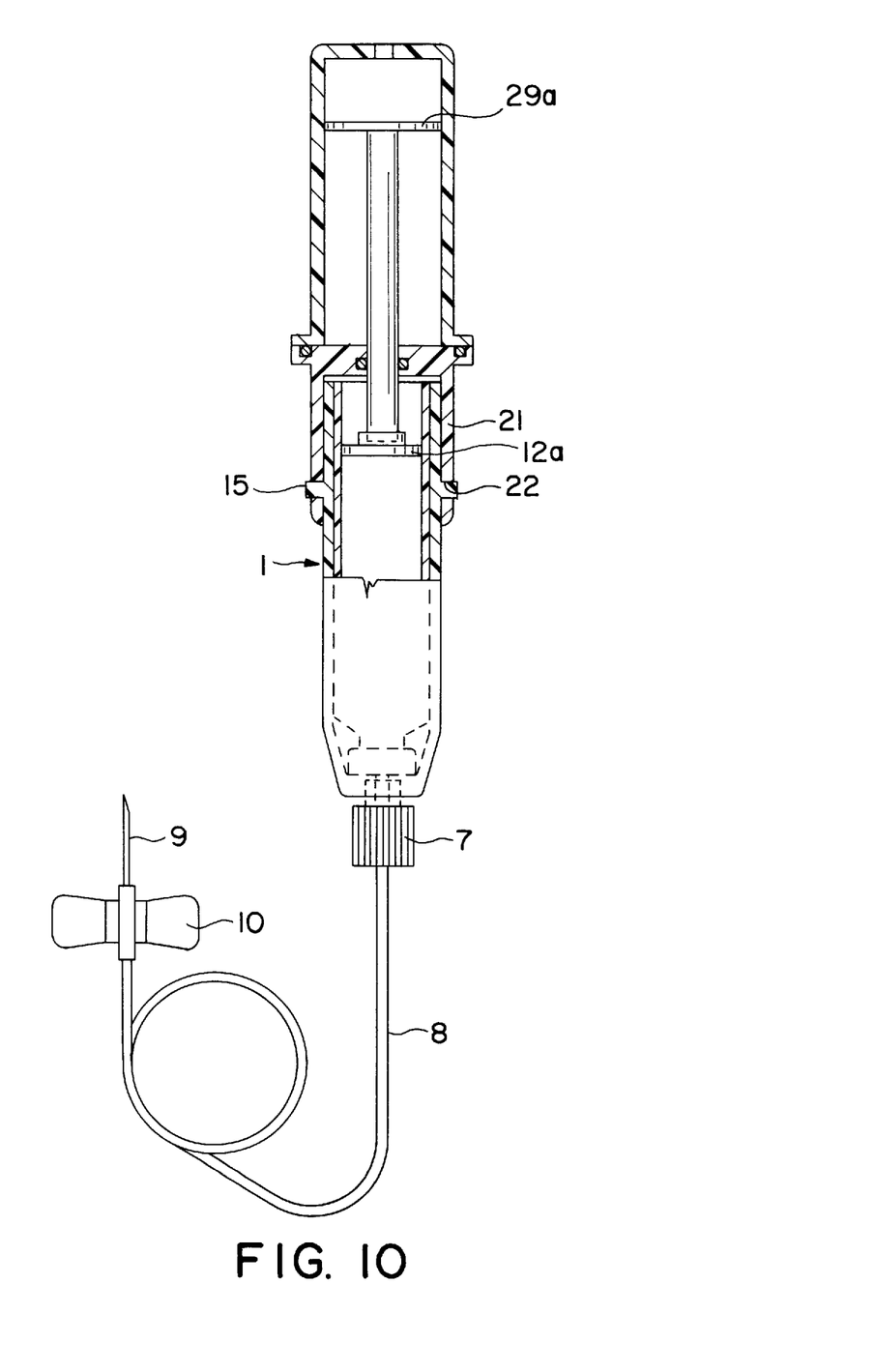
FIG. 10 represents a partial cross-sectional view of an embodiment of an apparatus according to the present invention that includes moveable walls that are membranes.

FIG. 10 shows an embodiment of the apparatus of the invention that differs from the embodiment shown in FIG. 3 by having as FIG. 10 shows an embodiment of the apparatus of the invention that differs from the embodiment shown in FIG. 3 by having as movable walls membranes 29a and 12a.

Figure 4:
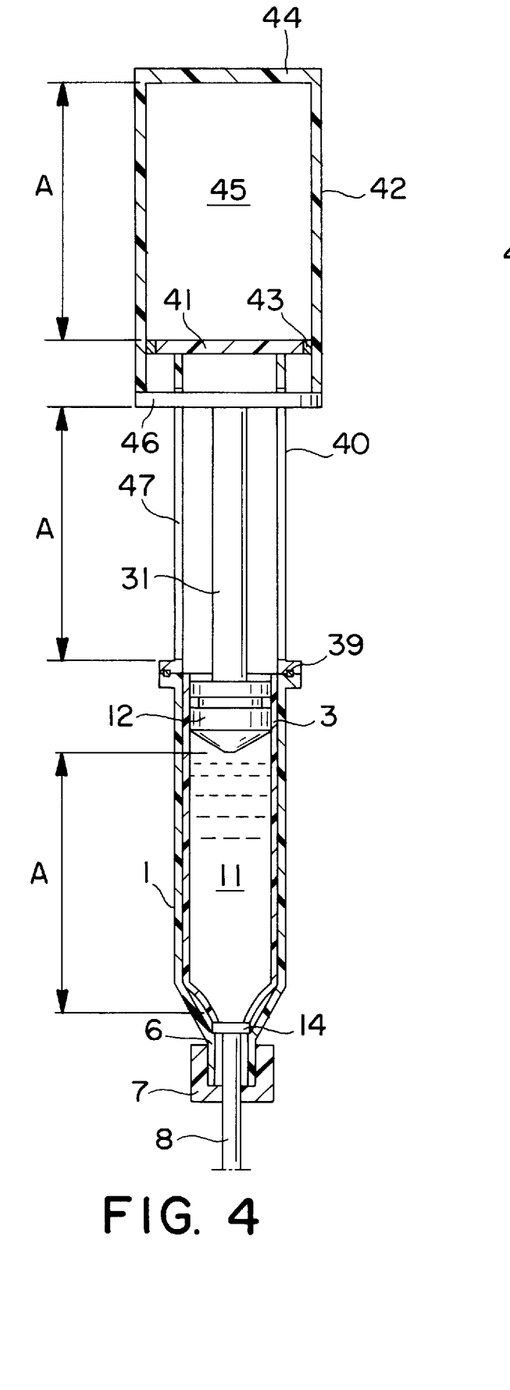
FIGS. 4 and 5 represent cross-sectional views of another embodiment of an apparatus according to the present invention in an assembled state illustrating the plunger in two different positions.
Figure 5:
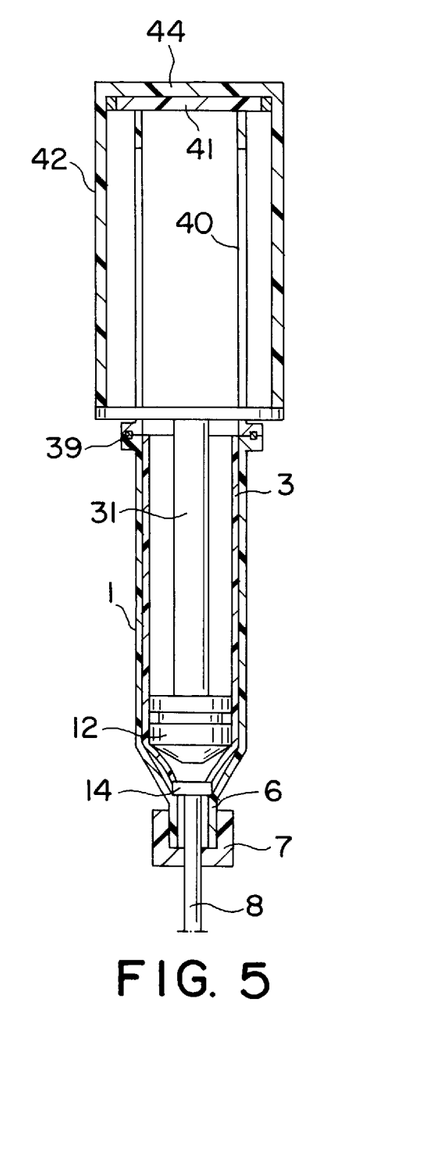

FIGS. 4 and 5 show another embodiment of the apparatus of the invention. Here, FIG. 4 shows the apparatus in its assembled state before administration, and FIG. 5 shows the assembled apparatus after completed administration of the liquid.

The delivery unit shown in FIGS. 4 and 5 may be the same as that shown in FIGS. 1 and 3, and comprises a sleeve 1, which contains an injection cartridge 3. The injection cartridge has a plunger or piston 12 at its rear end, and a conventional closure at its front end by a metal capsule 14. The sleeve 1 is provided at its front end with a threaded connecting tube 6, a connecting piece 7, and a flexible tube 8, which is in liquid connection with the interior of the cartridge 2, as described hereinbefore.

The power unit comprises a tubular sleeve 40, which is joined coaxially to the sleeve 1 of the delivery unit by means of a joint 39. This joint may be permanent or may be releasable, such as a bayonet lock or a threaded joint.

At its rear end, the tubular sleeve 40 is joined to a piston 41, which is slidably mounted in a cylinder 42. An airtight seal between the piston 41 and the internal wall of the cylinder 42 is assured by means of a sealing ring 43. The cylinder 42 is closed at its rear end by the wall 44 and defines and enclosed space 45.

At its front end, the cylinder 42 is connected to a bracket 46, which in its turn is connected to a connecting rod 31. The connecting rod 31 is arranged inside the tubular sleeve 40, and the bracket 46 may be T-shaped, the arms of the "T" extending through longitudinal slots 47 in the wall of the sleeve 40 to be joined to the front end of the cylinder 42. Other shapes of the bracket 46 are of course also possible. Thus, the ambient atmosphere has access to the interior of the tubular sleeve 40 and to the open front end of the cylinder 42, but the space 45 inside the cylinder 42 is closed off from the atmosphere by the piston 41.

Before the power unit is made ready for use, its parts are as shown in FIG. 5. Here, the tubular sleeve 40 is at its innermost position within the cylinder 42, and the piston 41 is resting against the end wall 44 of the cylinder. The space 45 in the cylinder 42 between the piston 41 and the end wall 44 is essentially zero. The connecting rod 31 is at its foremost position and protrudes from the tubular sleeve 40.

When the apparatus is to be made ready for use, a full injection cartridge 3 is inserted into the sleeve 1 and the tubular sleeve 40 is connected to the rear end of the sleeve 1 by means of the joint 39, while the connecting rod 31 is resting against the rear end of the plunger 12. In this operation, the connecting rod 31 is forced back into the tubular sleeve 40, and by means of the bracket 46 also forces the cylinder 42 backwards. As the piston 41 is fixedly attached to the rear end of the tubular sleeve 40, this means that there will be a relative movement between the piston 41 and the cylinder 42, such that a closed space 45 will be established. In this space 45, there will be a vacuum, as the piston 41 is sealed against the internal wall of the cylinder 42 by means of the sealing ring 43.

The pressure of the ambient atmosphere will now act to urge the piston 41 into the cylinder 42, and as a result of this, the connecting rod 31 will exert a pressure on the plunger 12 to force the liquid 11 out of the cartridge 3 through the tube 8. The liquid connection between the tube 8 and the interior of the cartridge 3 may be established, as described earlier, before or after the vacuum space 45 has been established.

When all of the liquid 11 in the cartridge 3 has been administered, the apparatus is in the state shown in FIG. 5. The tubular sleeve 40 is now fully retracted into the cylinder 42, and the piston 41 rests against the end wall 44. For this, the apparatus should be dimensioned such that the length of travel for the piston 41 in the cylinder 42 should be the same as the length of travel arranged for the plunger 12 in the cartridge 3, and it then folows that the length of travel for the bracket 46 in the slots 47 of the tubular sleeve 40 will also be the same. These distances are noted with "A" in FIG. 4.

When the cartridge 3 has been emptied, the connection 39 between the sleeve 1 and the tubular sleeve 40 may be released, and the power unit may be used for a further delivery after the used injection cartridge 3 has been replaced with a fresh one. If the apparatus is intended to be disposable, for one-time use only, the connection 39 may be permanent, and the whole apparatus is then discarded after use.

The embodiment shown in FIGS. 4 and 5 has the advantage that only one seal is necessary, between the piston and the cylinder, and there is no need for the connecting rod 31 to traverse a wall sealingly.

Figures 6, 7:
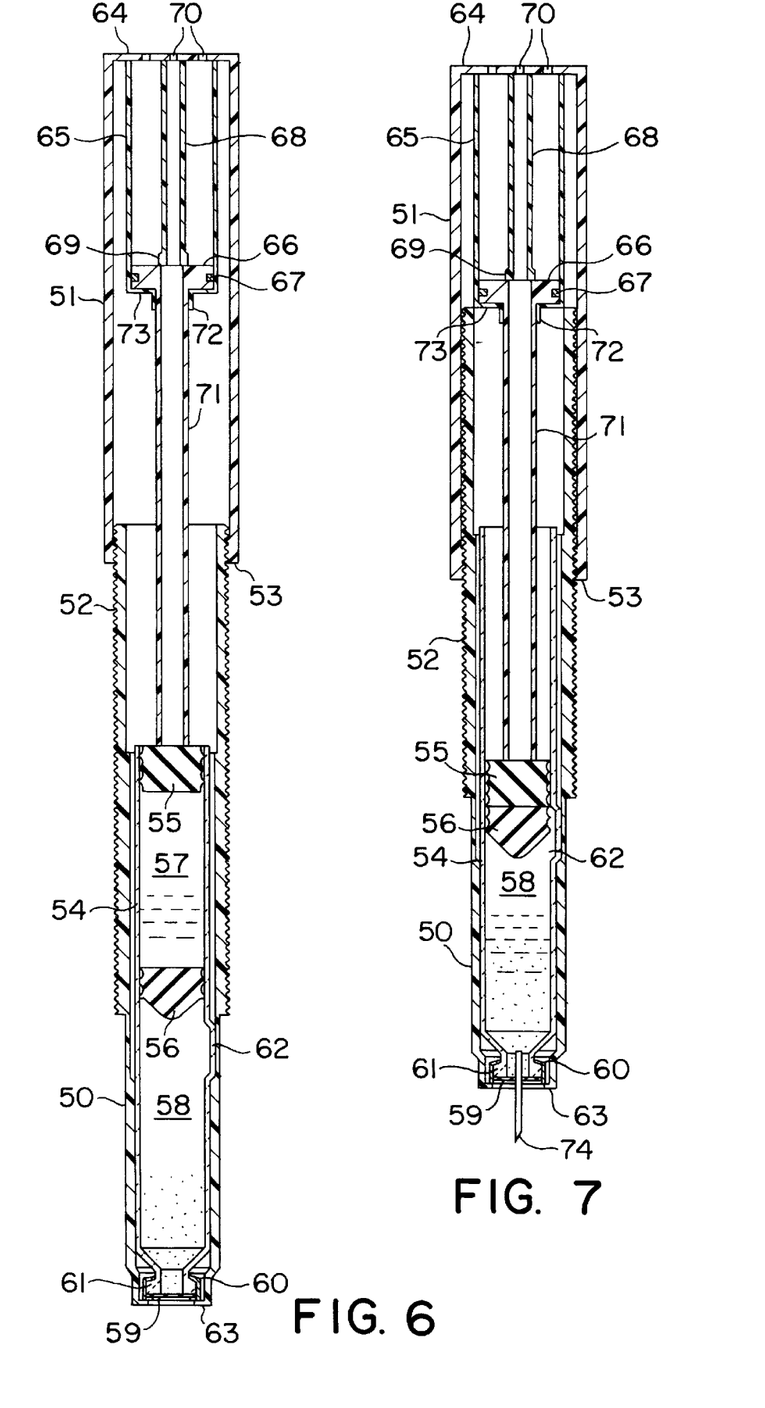
FIGS. 6–9 represent cross-sectional views of a still further embodiment of an apparatus according to the present invention that include a dual-chamber injection cartridge, illustrating successive stages of development and use for infection.
Figure 8:
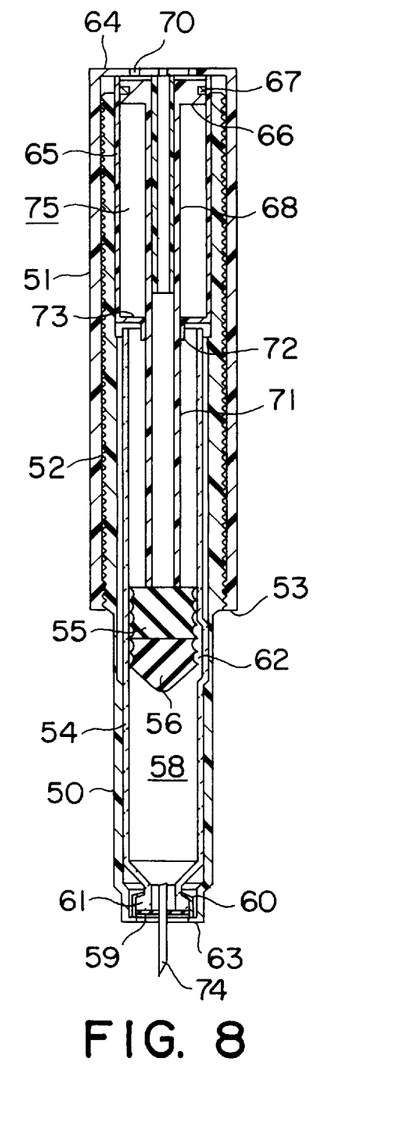
Figure 9:
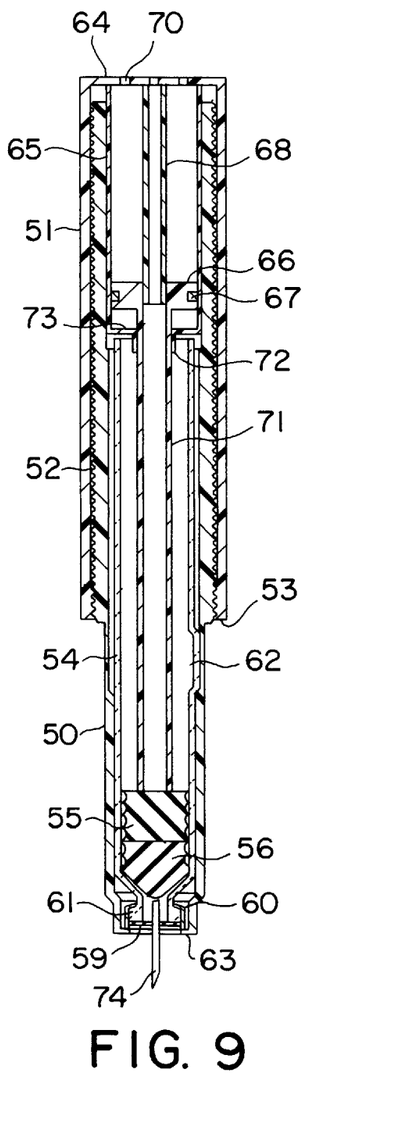

FIGS. 6 to 9 show a still further embodiment of an apparatus of the invention, wherein a dual-chamber injection cartridge is used. Here, FIG. 6 shows the apparatus with the cartridge in its place, but before the two components in the cartridge have been mixed. FIG. 7 shows the apparatus after the components in the cartridge have been mixed, and FIG. 8 shows the apparatus after the driving force vacuum has been established. FIG. 9, finally, shows the apparatus after the contents of the cartridge has been expelled by means of the vacuum driving force.

The apparatus shown in FIG. 6 comprises a front tubular sleeve 50 and a rear tubular sleeve 51, which are joined together by means of an external thread 52 on the front sleeve 50 and a matching internal thread 53 on the rear sleeve 51.

Inside the front sleeve 50, at its front end, this sleeve is arranged to receive a dual-chamber injection cartridge 54. This cartridge is of a conventional construction and comprises a rear piston 55 and a front piston 56, which between them define a rear chamber 57, which usually contains a liquid product. A front chamber 58, which usually contains a solid product, is defined between the front piston 56 and the front end of the cartridge, which is closed by a septum 59 which is held in place by a capsule 60 secured around a flange 61 at the bottleneck-shaped front end of the cartridge. In the wall of the cartridge is arranged a bypass channel 62. The dual-chamber cartridge as such is of a conventional type, and does not have to be described in further detail.

At its front end, the front sleeve 50 is provided with a flange 63, against which the front end of the cartridge 54 rests. The flange 63 also defines a hole in the front end, through which a liquid connection may be established with the interior of the cartridge 54 by means of a hollow needle or cannula.

The front sleeve 50 with the dual-chamber injection cartridge 54 arranged inside is the delivery unit of the apparatus of the invention.

The rear sleeve 51 is closed at its rear end by a wall 64. Inside the rear sleeve 51 is arranged a cylinder 65, which is attached to the inside of the rear end wall 64. In the cylinder is arranged a piston 66, which may be displaced axially inside the cylinder 65 and is sealed gas-tight against the cylinder wall by means of a sealing ring 67.

Inside the cylinder 65 is also arranged a tubular distance rod 68, which is attached to the inside of the rear wall 64 and is coaxial with the cylinder 65 and the rear sleeve 51. At its front end, the distance rod 68 is provided with a deformable flange 69, whose function will be described in more detail later.

The length of the distance rod 68 is such that when the piston 66 is in its foremost position, the front end of said distance rod with its deformable flange 69 will abut the rear face of the piston, and will thus hold the piston in said foremost position.

The rear end wall 64 of the rear sleeve 51 is provided with openings 70. Through these openings 70, the space in the cylinder 65 behind the piston 66 will be in connection with the outer atmosphere.

To the front face of the piston 66 is attached a tubular connecting rod 71. This connecting rod 71 goes through an opening 72 in a transversal wall 73 of the cylinder 65, and is coaxial with the rear sleeve 51. The connecting rod 71 is also in gas-sealing relationship with the opening 72 in the transversal cylinder wall 73. The length of the connecting rod 71 is such that when the apparatus has been assembled, the front end of said connecting rod will rest against the rear face of the rear piston 55 of the injection cartridge 54.

The inside bore of the connecting rod 71 extends through the piston 66 and has such a diameter that the distance rod 68 can be introduced into said bore. By the deformable flange 69, however, the distance rod 68 is prevented from entering into the bore of the connecting rod 71, as this flange has a larger diameter than that of said bore.

The rear sleeve 51 with its associated piston and cylinder arrangement is the power unit of the apparatus of the invention.

FIG. 7 shows the apparatus of FIG. 6 after the two components in the cartridge have been mixed. The rear sleeve 51 has now been screwed forward on the front sleeve 50 by means of the threads 52 and 53, and the connecting rod 71 has then pushed the rear piston 55 forward to a postion where it rest against the front piston 56. This front piston has also been moved forward, such that the bypass channel 62 is exposed, to allow the liquid in the rear chamber to flow over to the front chamber 58, where it is mixed with the solid product in said front chamber. As the distance rod 68 with its flange 69 rests against the rear face of the piston 66, this piston is prevented from moving backwards in the cylinder 65.

A hollow needle or cannula 74 has also been inserted through the hole in the front end of the front sleeve 50, to pierce the septum 59 and establish a liquid connection with the interior of the cartridge 54. This needle is connected to a tube (not shown), which at its other end is provided with an injection needle or cannula for administering an injection of infusion to a patient. The tube is also provided with flow restricting means, which in the stage shown in this figure are completely closed, so that no liquid can flow out from the cartridge 54. The apparatus is now ready for activating the power unit.

FIG. 8 shows the apparatus of FIG. 7 after the power unit of the apparatus has been activated. The rear sleeve 51 has been screwed fully forward on the front sleeve 50, the external thread 52 of which has a sufficient length to allow this. Also, the spacing between the outside of the cylinder 65 and the inside of the rear sleeve 51 must be sufficient to admit the rear part of the front sleeve 50. As the outflow of liquid through the needle 74 is blocked by the flow restricting means (not shown), the front and rear pistons 56 and 55, respectively, have not been moved further forward in the cartridge 54.

At the rear end of the connecting rod 71, the distance rod 68 has now entered into the bore of said connecting rod. This has been made possible by the deformable flange 69 yielding under the increased load on it by the piston 66, such that it no longer prevents the distance rod 68 from entering the bore of the tubular connecting rod 71.

This means that the piston 66 can now be moved rearward in relation to the cylinder 65. As the connecting rod 71 traverses the end wall 73 in a gas-sealing manner through the opening 72, a vacuum will be established in the space 75 in front of the piston 66. In the rear of the cylinder, on the other side of the piston 66, the cylinder is in connection with the outer atmosphere through the openings 70.

The deformability of the flange 69 is adjusted such that it will not yield when the cartridge 54 is readied for use by the mixing of the components therein, but will yield under the considerably greater effort necessary to establish the vacuum in the cylinder 65. Such properties of the flange 69 can be established by a person skilled in the art, by selecting suitable materials and dimensions on the basis of simple tests.

When the vacuum has been established in the space 75, the atmospheric pressure acting on the rear face of the piston 66 strives to move the piston 66 forward and, through the action of the connecting rod 71, also the pistons 55 and 56 of the cartridge 54, to expel the mixed product from the cartridge chamber 58 through the needle 74. However, as the outlet through the needle 74 is closed by the flow restriction means, the pistons 55 and 56 in the cartridge 54 cannot move forward, and therefore also not the piston 66 in the cylinder 65.

When the flow restricting means in the tube connected to the needle 74 are opened, the atmospheric pressure acting on the rear face of the piston 66 will urge this piston forward and, through the intermediary of the connecting rod 71, also the pistons 55 and 56 of the cartridge 54, to expel the product in the chamber 58 through the needle 74. The outflow rate from the cartridge 54 is governed by a suitable adjustment of the flow restricting means.

When the mixed product has been completely expelled from the cartridge, the apparatus will be in the state shown in FIG. 9. The piston 66 in the cylinder 65 has now been moved fully forward by the action of the atmospheric pressure on its rear face, and has moved the pistons 55 and 56 fully forward in the cartridge, through the action of the connecting rod 71, such that the injectable mixed product in the cartridge has been fully expelled through the needle 74.

The apparatus according to this embodiment of the invention may be supplied to the user in an assembled state, already containing the dual-chamber cartridge but before the contents of said cartridge have been mixed. It may also be supplied with the delivery unit and the power unit separated, with the user inserting an injection cartridge and assembling the apparatus immediately before use.

The apparatus is primarily intended for one-time use only and to be discarded after use, as the deformable flange 69 on the distance rod 68 will usually be permanently deformed, so that a re-use of the apparatus with a fresh cartridge will not be possible. However, it is also conciveable that said flange is deformable elastically, and will revert to its original shape when the apparatus is disassembled. In such a case, a re-use of the apparatus will be possible. Usually, however, a re-use is not desirable for safety reasons.

It is an important feature of the invention that the power unit and the delivery unit are joined together coaxially. In this way, the power unit will be actuated immediately when the two units are joined together, and the force of the piston will be transmitted in a linear direction from the power unit directly to the plunger in the delivery unit by means of the direct mechanical connection in the form of the rod 31. Thus, the movement of the piston 29, 41, the rod 31 and the plunger 12 will take place along a common axis.

In the preferred and shown embodiment of the invention, the power unit is arranged at the opposite end of the sleeve 1 from the outlet end with its opening 4. However, it is also possible to arrange the power unit at the outlet end of the sleeve 1. In such an embodiment, the mechanical coupling will be in the form of a linkage which connects the piston in the power unit with the plunger in the delivery unit, and a simple connecting rod is not possible. Therefore, such an embodiment is more complicated and less preferred.

The flow of the liquid is controlled by the restriction arranged in the flow path. As mentioned previously, this restriction may be constant and in the form of a capillary arranged in the connecting piece 7. In this case, the liquid starts flowing as soon as a pressure is applied on the plunger 12 of the injection cartridge 3. This will also serve to expel air from the tube 8 and the needle 9 before the administration to the patient starts.

The restriction may also be variable, and may, for instance, be arranged as a clamp on the tube 8. In this case, the flow path may initially be closed completely, and may then be opened gradually when the administration starts.

As mentioned previously, the injection cartridge may be a dual-chamber cartridge, containing the active compound and a liquid phase separated by a movable wall. In this case, the pressure exerted by the rod 31 on the plunger 12 will immediately start to move the plunger forwards, together with the liquid and the separating movable wall. When the movable wall has reached the bypass channel in the wall of the cartridge, the further movement of the plunger will force the liquid through the bypass channel into the front chamber to get into contact with the active substance, so that this substance will be dissolved. After all of the liquid has been forced over into the front chamber and the plunger has got into contact with the movable wall, the plunger and the movable wall will act together as a single plunger to force the liquid phase with the dissolved active substance out of the cartridge. Thus, it will be seen that the handling of the apparatus to make it ready for administering the liquid is essentially the same, irrespective of the type of injection cartridge used.

The restriction is usually set such that the liquid in the cartridge will be administered for a time of at least 30 minutes, and usually for one hour or more. These times, however, are not critical, and can be set within very wide limits, from about a second up to 24 hours or more, depending on the intended use. The size of the restiction to be used can easily be determined on the basis of routine tests.

When the contents of the cartridge 3 has been administered to the patient, the bayonet lock 15, 22 is released and the two sleeves 1, 21 are taken apart from each other. Under the influence of the atmospheric pressure, the piston 29 will then return to its lowest position in the cylinder 25. From the delivery unit, the injection cartridge is removed through the rear opening 2 and discarded. The connecting piece 7 is unscrewed from the connecting tube 6, so that the tube 8 with the hypodermic needle 9 and the needle at its other end for establishing a connection with the cartridge 3 may be removed and discarded. After a new cartridge has been inserted into the sleeve 1 and a new tube 8 has been connected with the cartridge, the apparatus is ready to be connected to the power unit again for a new delivery of liquid.

In a variant, the connecting piece 7 may be replaced by a threaded cap, which protects the outlet end of the sleeve 1 and prevents access to its inside. In this case, the connecting piece 7 with the tube 8 and its connecting needle are not attached to the sleeve 1 until immediately before the administering of the liquid is to take place. This gives added security, as the rubber septum of the injection cartridge 3 is not pierced until the liquid is to be administered, so that the risk of bacterial contamination is decreased.

Thus, the sleeve 1 of the delivery unit and the whole power unit may be re-used indefinitely, and they will not have to be extensively sterilized, as they will not get into contact with the liquid which is to be administered. The power unit is not dependent on any external power source, and the vacuum which constitutes its driving power is not established until immediately before the apparatus is to be used. Thus, the problems of a possible leakage are greatly diminished. Also, the driving force is largely independent of the ambient temperature. Both the delivery unit and the power unit are very simple in their construction, and are therefore inexpensive to fabricate. The injection cartridge used does not have to be of any special construction, but may be of a conventional design, with one or two chambers. This further contributes to keep the costs low.

In the foregoing, the apparatus of the invention has been shown and described as an embodiment wherein an injection cartridge is used within a sleeve. This is a preferred embodiment, but it is not the only one contemplated. It is also possible to arrange the sleeve 1 itself as a container or syringe for the liquid, which is then drawn into the container through a needle attached to the connecting piece 7, optinally via a tube 8, from a separate liquid reservoir. The liquid is drawn into the container by withdrawing the plunger 12 from a position near the outlet end with the connecting tube 6 to a position near the rear end of the container. For this, the plunger may have a threaded hole in the bottom of the depression 13, so that a threaded rod may be temporarily attached to aid in the pulling back of the plunger. In this embodiment, it is of course also possible that the connecting rod 31 itself is threaded at its outer end and fits into a threaded depression in the plunger 12. When the apparatus is to be made ready for use, the rod 31 is first threaded into the depression in the plunger 12, so that it aids in pulling the plunger up when liquid is to be drawn into the syringe. After this, the two sleeves are locked together as described previously, and the atmospheric pressure against the vacuum will then be transmitted to the plunger 12, so that it is urged outwards.

The choice of material for the apparatus is not critical, and a suitable material can easily be selected by anyone skilled in the art. In some embodiments, it is important that the apparatus can be easily sterilized, for instance by autoclaving at an elevated temperature of at least about 120° C. Various plastic materials are suitable, but also metallic materials may be used, such as stainless steel and aluminum alloys.

It is to be noted that the invention is not limited to the embodiments shown in the drawing and described in the foregoing specification. To a person skilled in the art, various other variants and modifications of the invention are possible without departing from the scope of the invention, as defined by the appended claims. For instance, the apparatus is not limited to a device for the administration of liquids parenterally to humans or animals, but it may be used in all cases where a controlled delivery of liquids is desirable, such as in various laboratory applications.

We claim:

1. An apparatus for the controlled delivery of a liquid having a delivery unit comprising a first liquid container having at least one movable wall and a liquid outlet; wherein said movable wall is connected to a mechanical coupling; and a power unit which comprises a second container having a front end, a rear end, at least one movable wall wherein a vacuum can be established, and a sleeve having a front end and a rear end wherein said sleeve is joined at its front end to said delivery unit and at its rear end is joined to said movable wall of the power unit, which movable wall is slidably mounted in said second container; wherein said second container is connected to said mechanical coupling; said second container being closed at its rear end and defining a closed space and wherein its front end provides access for the ambient atmosphere; and wherein said delivery unit and said power unit are connected together coaxially.

2. The apparatus of claim 1, characterized in that the container for the liquid constitutes a syringe for injection or infusion.

3. The apparatus of claim 2, characterized in that the syringe comprises a sleeve holding a cartridge for injection.

4. The apparatus of claim 3, characterized in that the cartridge has two chambers which are separated by a movable wall, and a bypass channel between the two chambers, said bypass channel becoming operative by the movement of said movable wall of said cartridge.

5. The apparatus of claim 1, wherein said liquid outlet is provided with a flow restriction.

6. The apparatus of claim 5, characterized in that the flow restriction is arranged as a constriction in the flow path of the liquid.

7. The apparatus of claim 5, characterized in that the restriction is variable.

8. The apparatus of claim 1, characterized in that the movable walls in the containers are pistons or plungers.

9. The apparatus of claim 1, characterized in that one or both of the movable walls is a membrane.

10. An apparatus for the controlled delivery of a liquid having a delivery unit comprising a first liquid container having at least one movable wall and a liquid outlet; wherein said movable wall is connected to a mechanical coupling; and a power unit which comprises a second container having a front end, a rear end, at least one movable wall wherein a vacuum can be established; wherein the movable wall of said power unit is connected to said mechanical coupling or wherein said power unit further comprises a sleeve having a front end and a rear end wherein said sleeve is joined at its front end to said delivery unit and at its rear end is joined to said movable wall of the power unit and said second container is connected to said mechanical coupling; and wherein said liquid container is a syringe for injection or infusion which comprises a front sleeve and a rear sleeve which are axially movable relative to each other for holding a cartridge that has a rear chamber and a front chamber which are separated by a movable wall, and a bypass channel between the rear and front chambers, said bypass channel becoming operative by the movement of said wall; of said cartridge and wherein a first piston is contained in said rear chamber and a second piston is contained in said front chamber; and a third piston is contained within said second container; and wherein said second container also includes limiting means for preventing said third piston from moving towards said second container until said first piston is in a position of resting against said second piston; and wherein said delivery unit and said power unit are connected together coaxially.

11. The apparatus of claim 10 wherein said liquid outlet is provided with a flow restriction.

12. The apparatus of claim 11, characterized in that the flow restriction is arranged as a constriction in the flow path of the liquid.

13. The apparatus of claim 11, characterized in that the restriction is variable.

14. The apparatus of claim 10 wherein said movable wall of said power unit is connected to said mechanical coupling.

15. The apparatus of claim 14 characterized in that the movable walls in the containers are pistons or plungers, and that the mechanical coupling is a piston rod, which connects the two pistons or plungers.

16. The apparatus of claim 10 wherein said limiting means is a distance rod.

17. The apparatus of claim 14 characterized in that one or both of the movable walls is a membrane.

* * * * *